(12) United States Patent
Stopek

(10) Patent No.: US 8,986,203 B2
(45) Date of Patent: Mar. 24, 2015

(54) SINGLE PORT DEVICE INCLUDING SELECTIVELY CLOSEABLE OPENINGS

(71) Applicant: Covidien LP, Mansfield, MA (US)

(72) Inventor: Joshua Stopek, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/524,449

(22) Filed: Oct. 27, 2014

(65) Prior Publication Data

US 2015/0045625 A1 Feb. 12, 2015

Related U.S. Application Data

(63) Continuation of application No. 14/324,599, filed on Jul. 7, 2014, now Pat. No. 8,894,575, which is a continuation of application No. 14/185,250, filed on Feb. 20, 2014, now Pat. No. 8,795,164, which is a continuation of application No. 12/887,802, filed on Sep. 22, 2010, now Pat. No. 8,684,918.

(60) Provisional application No. 61/248,035, filed on Oct. 2, 2009.

(51) Int. Cl.
*A61B 1/32* (2006.01)
*A61B 17/02* (2006.01)

(52) U.S. Cl.
CPC ..... *A61B 17/0218* (2013.01); *A61B 2017/0225* (2013.01)
USPC ......................................................... 600/215

(58) Field of Classification Search
USPC .................. 600/204–205, 221, 215
See application file for complete search history.

(56) References Cited

U.S. PATENT DOCUMENTS

| | | | |
|---|---|---|---|
| 3,855,997 A * | 12/1974 | Sauer ........................ | 600/573 |
| 5,211,181 A | 5/1993 | Delente | |
| 5,375,588 A | 12/1994 | Yoon | |
| 5,842,971 A | 12/1998 | Yoon | |
| 5,906,577 A | 5/1999 | Beane et al. | |
| 6,162,196 A | 12/2000 | Hart et al. | |
| 6,454,783 B1 | 9/2002 | Piskun | |
| 6,551,270 B1 | 4/2003 | Bimbo et al. | |
| 7,736,306 B2 | 6/2010 | Brustad et al. | |
| 7,798,898 B2 | 9/2010 | Luciano, Jr. et al. | |
| 8,684,918 B2 | 4/2014 | Stopek | |
| 8,795,164 B2 | 8/2014 | Stopek | |
| 8,821,390 B2 | 9/2014 | Kleyman | |

(Continued)

FOREIGN PATENT DOCUMENTS

| | | |
|---|---|---|
| AU | 2010200632 A1 | 9/2010 |
| EP | 0226026 A2 | 6/1987 |

(Continued)

OTHER PUBLICATIONS

European Search Report for corresponding EP 10251718 date of mailing is Jan. 28, 2010 (3 pages).

(Continued)

*Primary Examiner* — Sameh Boles

(57) ABSTRACT

A surgical port includes a port body having a lumen extending therethrough and a plate having an opening. The port body may be made from foam. The port is configured such that rotation of the plate with respect to the port body aligns the opening and lumen defining a passage therethrough for the insertion of surgical instruments.

14 Claims, 3 Drawing Sheets

(56) References Cited

U.S. PATENT DOCUMENTS

| | | |
|---|---|---|
| 8,894,575 B2 | 11/2014 | Stopek |
| 2005/0096695 A1 | 5/2005 | Olich |
| 2005/0148823 A1 | 7/2005 | Vaugh et al. |
| 2006/0161050 A1 | 7/2006 | Butler et al. |
| 2006/0229501 A1 | 10/2006 | Jensen et al. |
| 2006/0247499 A1 | 11/2006 | Butler et al. |
| 2008/0255519 A1 | 10/2008 | Piskun et al. |
| 2009/0036745 A1 | 2/2009 | Bonadio et al. |
| 2009/0093752 A1 | 4/2009 | Richard et al. |
| 2009/0326332 A1 | 12/2009 | Carter |
| 2011/0166423 A1 | 7/2011 | Farascioni et al. |
| 2011/0251463 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0130184 A1 | 5/2012 | Richard |

FOREIGN PATENT DOCUMENTS

| | | |
|---|---|---|
| EP | 0950376 A1 | 10/1999 |
| EP | 1774918 A1 | 4/2007 |
| EP | 2044889 A1 | 4/2009 |
| WO | 97/33520 | 9/1997 |
| WO | 99/16368 | 4/1999 |
| WO | 01/49363 | 7/2001 |
| WO | 2008/042005 | 4/2008 |
| WO | 2008/093313 | 8/2008 |

OTHER PUBLICATIONS

European Search Report for EP10 25 0885—completion date Aug. 18, 2010—which application corresponds to U.S. Appl. No. 12/754,638, filed Apr. 6, 2010.
European Search Report EP08253236 dated Feb. 10, 2009.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
Australian Examination Report dated Apr. 5, 2013 issued in AU2010226925.

* cited by examiner

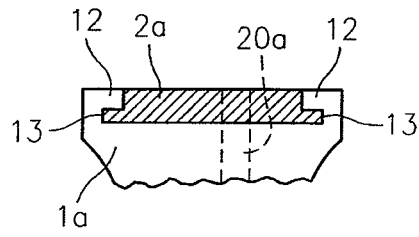
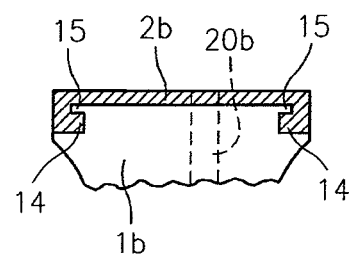
FIG. 3a    FIG. 3b
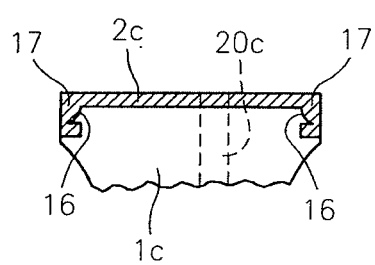
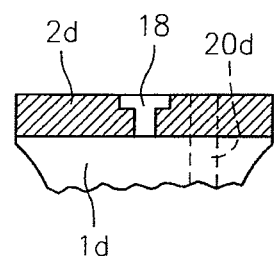
FIG. 3c    FIG. 3d
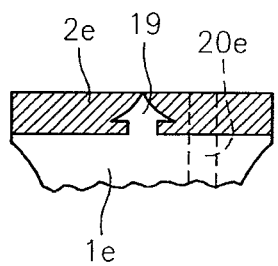
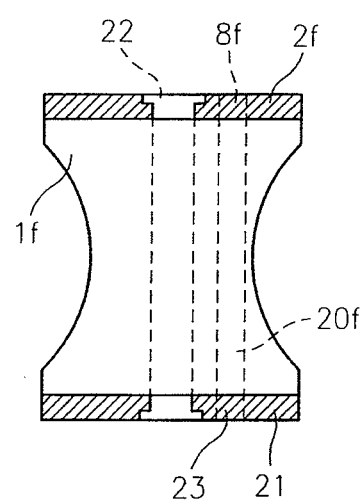
FIG. 3e    FIG. 3f

SINGLE PORT DEVICE INCLUDING SELECTIVELY CLOSEABLE OPENINGS

CROSS-REFERENCE TO RELATED APPLICATIONS

This application is a continuation of U.S. patent application Ser. No. 14/324,599, filed on Jul. 7, 2014, now U.S. Pat. No. 8,894,575, which is a continuation of U.S. patent application Ser. No. 14/185,250, filed on Feb. 20, 2014, now U.S. Pat. No. 8,795,164, which is a continuation of U.S. patent application Ser. No. 12/887,802, filed on Sep. 22, 2010, now U.S. Pat. No. 8,684,918, which claims priority to and benefit from U.S. Provisional Patent Application No. 61/248,035, filed Oct. 2, 2009. The entire content of each of the applications identified above is incorporated by reference herein.

BACKGROUND

1. Technical Field

The present disclosure relates to seals for use in surgical procedures. More particularly, the present disclosure relates to a seal anchor member adapted for insertion into an incision or opening in tissue.

2. Discussion of Related Art

Today, many surgical procedures are performed through small incisions in the skin, as compared to the larger incisions typically required in traditional procedures, in an effort to reduce both trauma to the patient and recovery time. Generally, such procedures are referred to as endoscopic, unless performed on the patient's abdomen, in which case the procedure is referred to as laparoscopic. Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to minimize or inhibit the escape of the insufflation gases and the deflation or collapse of the enlarged surgical site.

To this end, various valves and seals are used during the course of minimally invasive procedures. However, a continuing need exists for a seal anchor member that can be inserted directly into the incision in tissue and that can accommodate a variety of surgical objects while maintaining the integrity of an insufflated workspace.

SUMMARY

In accordance with various embodiments, the present disclosure is directed toward a surgical port having a compliant port body having at least one lumen extending therethrough. A plate may be moveably connected to the port body. The plate defines an opening that is selectively alignable with the at least one lumen. The surgical plate may be disposed in a substantial perpendicular relationship to the lumen. The plate may be rotatably moveable relative to the port body. The plate may be disposed on a proximal surface, a distal surface, or both surfaces of the port body. The plate may be movable through a discrete number of positions relative to the port body. Where when the plate is in a first position relative to the port body, all of the at least one opening of the plate is in complete alignment with the at least one lumen of the port body and when the plate is in a second position relative to the port body, less than all of the at least one opening of the plate is in partial alignment with the at least one lumen of the port body. The port body may be formed of foam.

In accordance with various example embodiments, the present disclosure is also directed towards a surgical port including a compliant port body having a lumen extending therethrough. The surgical port includes a plate rotatably disposed relative to the lumen, the plate defining an opening that, at least once in the plate's rotational path, is selectively alignable with the lumen so as to define a passage through the lumen and the opening for a surgical instrument. The surgical port may also include a first structure configured to facilitate rotation of the plate relative to a longitudinal axis of the port body. The first structure may comprise a pin. The surgical port may also include a second structure configured to maintain the relative position of the plate. The second structure maybe a shoulder disposed at the circumference of the plate which abuts a retaining shoulder on the body of the laparoscopic port. The plate may be located on a proximal surface of the port body. The surgical port may also include a second plate, and the second plate may be located on a distal surface of the port body. The plate and the second plate may be connected to each other so as to be moveable together relative to the port body. There may be multiple positions along a rotational path of the plate relative to the body such that a unique configuration of lumens therebetween is defined at each position. The plate may have a substantially arcuate convex profile. The plate may have a substantially arcuate concave profile. The plate may define an indentation along the circumference of the plate to facilitate rotation of the plate relative to the body.

BRIEF DESCRIPTION OF THE DRAWINGS

Various embodiments of the present disclosure are described herein with references to the drawings, wherein;

FIG. 3a is a cut-away plan view of a port having a plate retained by a circumferential shoulder disposed on a port body;

FIG. 3b is a cut-away plan view of a port having a plate retained by a circumferential shoulder disposed on a plate;

FIG. 3c is a cut-away plan view of a port having a plate retained by an angled circumferential shoulder disposed on a plate;

FIG. 3d is a cut-away plan view of a port having a plate retained by a pin;

FIG. 3e is a cut-away plan view of a port having a plate retained by a conical protrusion; and FIG. 3f is a cut-away plan view of a port having a distal plate and a connecting pin.

DETAILED DESCRIPTION

Figure 1:
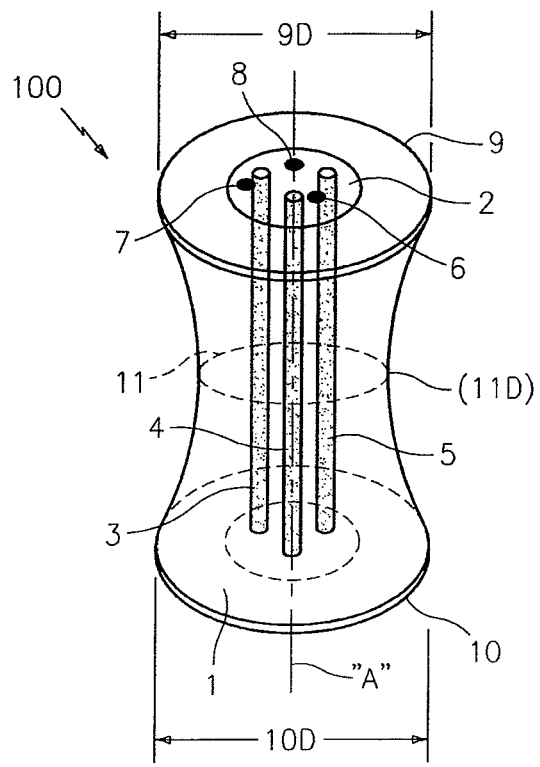
FIG. 1 is a perspective view of an embodiment of a port, according to an example embodiment of the present invention.

While embodiments of the present disclosure are susceptible to various modifications and alternative constructions, certain illustrated embodiments thereof have been shown in the drawings and will be described below in detail. It should be understood, however, that there is no intention to limit the embodiments of the present disclosure to the specific form disclosed, but, on the contrary, the embodiments are intended to cover all modifications, alternative constructions, and equivalents falling within the spirit and scope of the present disclosure as defined in the claims.

In the drawings and in the description which follows, in which like references numerals identify similar or identical elements, the term "proximal" will refer to the end of the apparatus which is closest to the clinician during use, while the term "distal" will refer to the end which is furthest from the clinician, as is traditional and known in the art.

With reference to FIG. 1, an embodiment of the presently disclosed access port is shown. The seal anchor member 100 includes a body 1 which is a temporary percutaneous implant configured to traverse the skin of a patient. Although the embodiment in FIG. 1 shows a percutaneous implant, it is contemplated that body 1 could traverse any biological barrier to provide selective communication between the volumes on opposing sides of the barrier. These include inter and intra organ barriers as well as systemic barriers within the body. It is further envisioned that the surgical port presently disclosed may be used in a naturally occurring orifice.

Figure 1A:
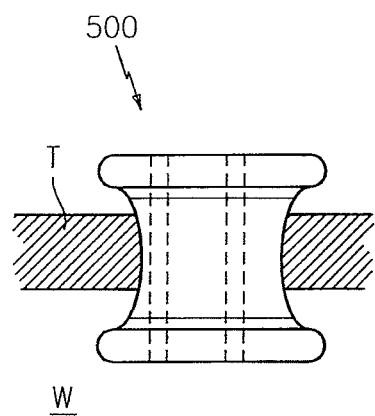
FIG. 1a is a side perspective view of a related seal anchor member of shown in the expanded condition and subsequent to its insertion into an incision.

The body 1 of the access port has a generally cylindrical form with a proximal surface 9 having a first diameter 9D and a distal surface 10 having a second diameter 10D with a medial plane 11 having a third diameter 11D disposed therebetween such that third diameter 11D is less than second diameter 10D and first diameter 9D defining a profile which narrows near the medial plane and widens at the proximal surface 9 and distal surface 10, thereby defining a generally hourglass configuration. An example of an access port is disclosed by commonly assigned U.S. patent application Ser. No. 12/244,024, filed on Oct. 2, 2008 which is incorporated by reference in its entirety herein and illustrated in FIG. 1a as seal member 500 extending through an opening W in body tissue T.

Although FIG. 1 shows proximal surface 9 and distal surface 10 as planar, it is contemplated that the profile of either surface could be arcuate such that the surface is concave to facilitate the placement of surgical implements and reduce the likelihood of tearing the surface when instruments are angulated or convex to facilitate the removal of fluid from the surface.

It is further contemplated that body 1 is composed of a substantially compliant or compressible material such that when body 1 is inserted into an incision, the tissue disposed along the sides of the incision compresses body 1 with the resultant restorative force between body 1 and the tissue defining a sealing pressure therebetween. The sealing pressure forms a substantially fluid tight seal with its surrounding tissue which separates the volumes which body 1 traverses, e.g. between an insufflated cavity and the extra-corporeal environment.

A plurality of lumens 3, 4, and 5 traverses body 1 parallel to a longitudinal axis "A." Lumens 3, 4, and 5 may be configured to allow fluid communication between ends 9 and 10 or the insertion of surgical instruments (e.g. cannulas, trocars, endoscopes, etc.) therethrough.

As shown in FIG. 1, a plate 2 is disposed on proximal surface 9. Further, plate 2 and has openings 6, 7, and 8 extending therethrough.

Figure 2A:
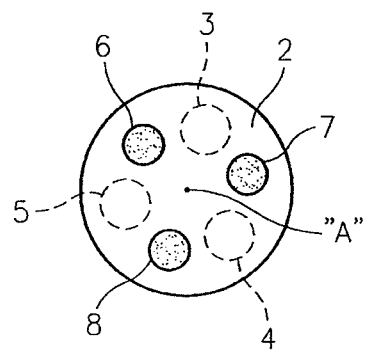
FIG. 2a is a top view of an embodiment of a port insert in a closed configuration.
Figure 2B:
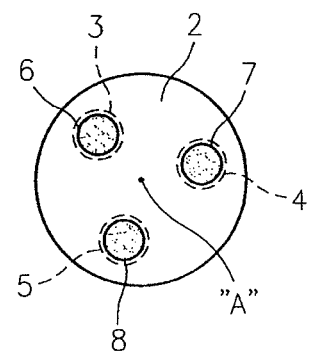
FIG. 2b is a top view of the port of FIG. 2a in an open configuration.

As shown in FIG. 2b, plate 2 may be rotated relative to body 1 about the longitudinal axis "A" to an "open" position wherein openings 6, 7, and 8 and lumens 3, 4, and 5 align defining passages therebetween.

As shown in FIG. 2a, plate 2 may be rotated relative to body 1 about the longitudinal axis "A" such that the holes 6, 7, and 8 and lumens 3, 4, and 5 are configured in a "closed" position wherein no holes align with any lumen thereby obscuring the passage previously defined therebetween.

Figure 2C:
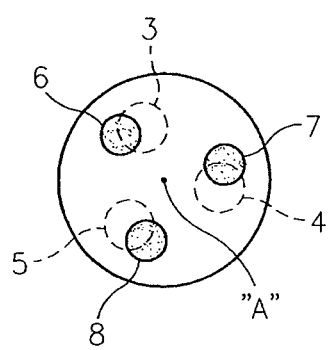
FIG. 2c is a top view of the port of FIGS. 2a and 2b in an intermediate configuration.

As shown in FIG. 2c, plate 2 may be rotated relative to body 1 about the longitudinal axis "A" such that the holes 6, 7, and 8 and lumens 3, 4, and 5 are configured in a transition or intermediate position wherein holes 6, 7, and 8 partially align with lumen 3, 4, and 5 thereby partially obscuring the passage previously defined therebetween.

It is further contemplated that there may be a plurality of holes and lumens in a specific arrangement corresponding to a plurality of positions along the rotational path of the plate. When so configured, rotation of the plate relative to the body about the longitudinal axis "A" to each unique position defines a unique configuration of passages which traverse the port in terms of both number and location of the lumens. For example, the holes disposed the plate and body may be arranged in a pentagon centered at a position other than the longitudinal axis "A". Consequently, if the plate is then rotated relative to the body about longitudinal axis "A", there will be a first position in which two pairs of holes and lumens on the plate and body align defining two passages therebetween. Similarly, there will be a second position, in which a different hole and lumen on the plate and body will align defining only one passage.

It is further contemplated that there may be a spring or other biasing device disposed in the port 100 to bias the plate 2 toward a neutral position when no force is applied such that there is a passage between the plate 2 and body 1 in the neutral position.

Alternatively, there may be a spring or other biasing device disposed in the port 100 to bias plate 2 toward a neutral position such that when no force is applied holes 6, 7, and 8 and lumens 3, 4, and 5 do not align thereby obscuring the passage previously defined therebetween.

In an embodiment shown in FIG. 3a, a body 1a has a stepped retaining shoulder 12 configured to abut a stepped ring 13 on a plate 2a such that plate 2a is retained relative to body 1 while being able to rotate relative to an axis parallel to a lumen 20a.

It is further contemplated, as shown in FIG. 3b, that a plate 2b has a stepped retaining shoulder 15 configured to abut a stepped ring 14 on a body 1b such that plate 2b is retained relative to body 1b while being able to rotate relative to an axis parallel to a lumen 20b.

It is further contemplated, as show in FIG. 3c, that a plate 2c has an angled stepped retaining shoulder 17 configured to abut an angled stepped ring 16 on a body 1c such that plate 2c is retained relative to body 1c while being able to rotate relative to an axis parallel to a lumen 20c.

It is further contemplated, as show in FIG. 3d, that there is a pin 18 which traverses plate 2 and a body 1d such that a plate 2d is retained relative to body 1 while being able to rotate relative to an axis parallel to lumen a 20d.

It is further contemplated, as show in FIG. 3e, that a body 1e has a substantially conical or frustoconical protrusion 19 which traverses a plate 2e such that plate 2e is retained relative to body 1e while being able to rotate relative to an axis parallel to a lumen 20e.

It is further contemplated, as shown in FIG. 3f, that a body 1f includes a proximal plate 2f having hole 8f, a distal plate 21 having a hole 23, and a traverse pin 22, and a lumen 20f. Traverse pin 22 couples the movement of distal plate 21 and proximal plate 2f such that hole 23 is aligned with lumen 20f when proximal hole 8f aligns with a lumen 20f defining a passage therebetween.

It is further contemplated that the axis about which plate 2 rotates is eccentric relative to plate 2 and body 1. It is further contemplated that, in various embodiments of the present invention, the seal anchor member 100 mat include multiple plates, each plate separately disposed so as to selectively cover and uncover different lumen, thereby providing a surgeon with additional flexibility, e.g., to cover a first lumen while leaving an instrument disposed within a second lumen, etc.

The use and function of seal anchor member 100 will be discussed during the course of a typical minimally invasive procedure.

Initially, the seal anchor member 100 is inserted into a tissue tract using known surgical techniques. Either subsequent or prior to the aforementioned insertion procedure, plate 2 on body 1 is configured in a first position, such that no holes on plate 2 align with any lumen disposed in body 1 thereby obscuring the lumen. In the course of this procedure, an operator may rotate plate 2 about the longitudinal axis "A" relative to body 1 into a second position such that one or more holes on plate 2 correspond to lumens on body 1 to define one or more passages therethrough. Thereafter, laparoscopic and endoscopic surgical instruments known in the art may be inserted into the lumen in order to carry out a surgical procedure.

During the course of the surgical procedure, an operator may replace or remove the instruments disposed in the port insert as needed.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

Those skilled in the art, having the benefit of the teachings of the present invention as herein and above set forth, may effect modifications thereto. Such modifications are to be construed as lying within the scope of the present invention, as defined by the appended claims.

Although specific features of the single port device are shown in some of the drawings and not in others, this is for convenience only as each feature may be combined with any or all of the other features in accordance with the aspects of the present disclosure. Other embodiments will occur to those skilled in the art and are within the following claims.

What is claimed is:

1. A surgical access port comprising: a compliant longitudinal port body having a proximal end and a distal end, the complaint port body defining a longitudinal axis and a first lumen extending through the proximal and distal ends; and a plate rotatable about and longitudinally fixed relative to the longitudinal axis, the plate defining an opening that is selectively alignable with the first lumen, wherein the first lumen defines a first lumen axis that is parallel to and offset from the longitudinal axis of the port body.

2. The surgical access port according to claim 1, wherein the plate is rotatably connected to the proximal end of the port body.

3. The surgical access port according to claim 1, wherein the plate is rotatably connected to the distal end of the port body.

4. The surgical access port according to claim 1, wherein the plate is disposed in perpendicular relation to the first lumen.

5. The surgical access port according to claim 1, wherein the plate has a first position relative to the port body, wherein in the first position the opening of the plate is in partial alignment with the first lumen of the port body.

6. The surgical access port according to claim 5, wherein the plate has a second position relative to the port body, wherein in the second position the opening of the plate is in complete alignment with the first lumen of the port body.

7. The surgical access port according to claim 1, wherein the complainant port body defines a second lumen between the proximal and distal ends, and wherein the opening is selectively alignable with the second lumen.

8. The surgical access port according to claim 7, wherein the plate has a third position to the port body, wherein in the third position, the opening is in partial alignment with the second lumen of the port body and offset from the first lumen of the port body.

9. The surgical access port according to claim 1, wherein the longitudinal axis of the port body passes through a center point of the first plate.

10. A surgical access port comprising: a compliant longitudinal port body having a proximal end and a distal end, the complaint port body defining a longitudinal axis and a lumen extending through the proximal and distal ends; and a first plate rotatably connected to the proximal end of the complaint port body, the first plate rotatably about and longitudinally fixed relative to the longitudinal axis, the first plate defining a first plate opening that is selectively alignable with the lumen; and a second plate rotatably connected to the distal end of the complaint port body, the second plate rotatably about and longitudinally fixed relative to the longitudinal axis, the second plate defining a second plate opening that is selectively alignable with the lumen, wherein the lumen defines a lumen axis that is parallel to and offset from the longitudinal axis of the port body.

11. The surgical access port according to claim 10, further comprising a structure coupled to the first and second plates to align the first plate opening with the second plate opening.

12. The surgical access port according to claim 11, wherein the structure is disposed about the longitudinal axis of the port body.

13. The surgical access port according to claim 11, wherein the structure passes through the first and second plates.

14. The surgical access port according to claim 11, wherein the structure is a pin extending through the port body.

* * * * *

UNITED STATES PATENT AND TRADEMARK OFFICE
CERTIFICATE OF CORRECTION

| | |
|---|---|
| PATENT NO. | : 8,986,203 B2 |
| APPLICATION NO. | : 14/524449 |
| DATED | : March 24, 2015 |
| INVENTOR(S) | : Joshua Stopek |

Page 1 of 1

It is certified that error appears in the above-identified patent and that said Letters Patent is hereby corrected as shown below:

In the Claims

Claim 10, line 6, change "rotatably" to -- rotatable --;

Claim 10, line 10, change "rotatably" to -- rotatable --.

See replacement claim 10 below:

10. A surgical access port comprising:

a compliant longitudinal port body having a proximal end and a distal end, the complaint port body defining a longitudinal axis and a lumen extending through the proximal and distal ends; and a first plate rotatably connected to the proximal end of the complaint port body, the first plate rotatable about and longitudinally fixed relative to the longitudinal axis, the first plate defining a first plate opening that is selectively alignable with the lumen; and a second plate rotatably connected to the distal end of the complaint port body, the second plate rotatable about and longitudinally fixed relative to the longitudinal axis, the second plate defining a second plate opening that is selectively alignable with the lumen, wherein the lumen defines a lumen axis that is parallel to and offset from the longitudinal axis of the port body.

Signed and Sealed this
Eighteenth Day of August, 2015

Michelle K. Lee
*Director of the United States Patent and Trademark Office*